US012446654B2

(12) United States Patent
Cormier

(10) Patent No.: US 12,446,654 B2
(45) Date of Patent: Oct. 21, 2025

(54) AUXILIARY OR INTEGRATED INNER SOLE STRUCTURE FOR FOOTWEAR

(71) Applicant: Marc Cormier, Montreal (CA)

(72) Inventor: Marc Cormier, Montreal (CA)

( * ) Notice: Subject to any disclaimer, the term of this patent is extended or adjusted under 35 U.S.C. 154(b) by 0 days.

(21) Appl. No.: 18/685,862

(22) PCT Filed: Dec. 30, 2022

(86) PCT No.: PCT/CA2022/051908
§ 371 (c)(1),
(2) Date: Feb. 22, 2024

(87) PCT Pub. No.: WO2023/122836
PCT Pub. Date: Jul. 6, 2023

(65) Prior Publication Data

US 2024/0260714 A1 Aug. 8, 2024

Related U.S. Application Data

(60) Provisional application No. 63/295,572, filed on Dec. 31, 2021, provisional application No. 63/295,568, filed on Dec. 31, 2021.

(51) Int. Cl.
*A43B 17/00* (2006.01)
*A43B 5/00* (2022.01)
(Continued)

(52) U.S. Cl.
CPC ............ *A43B 13/125* (2013.01); *A43B 5/001* (2013.01); *A43B 7/1405* (2013.01); (Continued)

(58) Field of Classification Search
CPC ... A43B 7/1405; A43B 7/1415; A43B 7/1485; A43B 13/386; A43B 17/00; A43B 17/006
(Continued)

(56) References Cited

U.S. PATENT DOCUMENTS 2,468,264 A * 4/1949 Katz .................... A43B 7/1415 36/147
2,660,814 A * 12/1953 Ritchey .................. A43B 7/142 36/80

(Continued)

*Primary Examiner* — Marie D Bays
(74) *Attorney, Agent, or Firm* — PRAXIS

(57) ABSTRACT

An inner sole structure for being mounted inside footwear for engagement by the foot comprises a middle sole part covered by a top part. The middle sole part defines has a thickness providing for supporting the foot and defines a longitudinal channel devoid of any material therein and defining an opening covered by the top sole part. When the inner sole structure is inside the footwear and engaged by the foot, the longitudinal channel is positioned under the foot of the wearer and is aligned with a longitudinal portion of the foot corresponding to a plantar fascia position of the foot to avoid tension against this foot portion. The inner sole structure comprises a support element for being mounted to an inner sole part of the footwear to be engaged by the foot. The support member is positioned to be engaged by a region of the foot corresponding to a position extending between at least near a fifth metatarsal rear end position of the foot to a heel bone position of the foot for providing stability to the foot for controlled supination.

20 Claims, 10 Drawing Sheets

(51) Int. Cl.

| | |
|---|---|
| ***A43B 7/1405*** | (2022.01) |
| ***A43B 7/1415*** | (2022.01) |
| ***A43B 13/12*** | (2006.01) |
| ***A43B 13/14*** | (2006.01) |
| ***A43B 13/38*** | (2006.01) |
| ***A43B 21/32*** | (2006.01) |
| *A43B 3/12* | (2006.01) |
| *A61F 5/14* | (2022.01) |

(52) U.S. Cl.
CPC .......... *A43B 7/1415* (2013.01); *A43B 13/141* (2013.01); *A43B 13/146* (2013.01); *A43B 13/386* (2013.01); *A43B 17/006* (2013.01); *A43B 21/32* (2013.01); *A43B 3/128* (2013.01); *A61F 5/14* (2013.01)

(58) Field of Classification Search
USPC ........................................................ 36/43, 44
See application file for complete search history.

(56) References Cited

U.S. PATENT DOCUMENTS

| | | | | | |
|---|---|---|---|---|---|
| 4,633,598 | A * | 1/1987 | Moronaga | A43B 13/40 36/44 |
| 4,777,739 | A * | 10/1988 | Hiles | A43B 7/1415 36/43 |
| 5,611,153 | A * | 3/1997 | Fisher | A43B 7/143 36/43 |
| 5,625,965 | A * | 5/1997 | Blissett | A43B 13/38 36/43 |
| 2015/0096192 | A1* | 4/2015 | McClaskey | A43B 13/386 36/44 |
| 2015/0157089 | A1* | 6/2015 | Schumacher | A43B 3/0057 36/25 R |
| 2017/0224050 | A1* | 8/2017 | Schouwenburg | A61F 5/0111 |
| 2017/0295883 | A1* | 10/2017 | Frey | A43B 7/1445 |
| 2021/0274886 | A1* | 9/2021 | Morsell | A61F 5/14 |

* cited by examiner

AUXILIARY OR INTEGRATED INNER SOLE STRUCTURE FOR FOOTWEAR

CROSS-REFERENCE TO RELATED APPLICATIONS

The present application claims priority on U.S. Provisional Patent Application Ser. No. 63/295,568 filed on Dec. 31, 2021 and on U.S. Provisional Patent Application Ser. No. 63/295,572 filed on Dec. 31, 2021, both of which are incorporated herein by reference in their entirety.

TECHNICAL FIELD

The present disclosure generally relates to footwear. More particularly, but not exclusively, the present disclosure relates to an auxiliary or integrated inner sole structure for footwear.

BACKGROUND

The background of the disclosure will be discussed herein with referecnt to FIGS. 1-7.

Quality footwear is important to protect users from foot injuries such as plantar fasciitis and other injuries. Footwear includes shoes, slippers, sandals, boots, orthosis, and the like as is understood in the art. The sole of a footwear comprises an outsole which touches the ground and an insole which is directly the foot of the wearer. The portion between the outsole and insole is referred to as the midsole. The insole (often referred to as the footbed) sits directly beneath the foot and provides cushioning in areas of the foot and also absorbs moisture away. Insoles can be taken out of a shoe and be replaced with new ones that suits the wearer's movement. The midsole is the material or sole part sandwiched between the insole and the outsole providing absorption, flex support and added cushioning.

Indeed, the outer sole part generally refers to the external part of the sole that is exposed to the ground surface and/or directly engages therewith and the inner sole part generally refers to the portion the sole that is opposite the outer sole and is engaged fully or partially by the foot or is beneath the surface directly engaged by the foot providing additional cushion, comfort support or working synergistically to with the surface directly engaged by the foot for enhancement thereof. Thus, the inner sole can include the insole and the midsole region as is understood in the art.

With reference to FIG. 1, which shows the anatomy of a foot F1, plantar fasciitis 1 is one of the most common causes of heel pain. It involves inflammation of a thick band of tissue that runs across the bottom of the foot and connects the heel bone to the toes (plantar fascia 3). Plantar fasciitis commonly causes stabbing pain that usually occurs with your first steps in the morning. Plantar fasciitis is more common in runners. People who are overweight and those who wear shoes with inadequate support also have an increased risk of plantar fasciitis. The plantar fascia also known as plantar aponeurosis is in the shape of a bowstring, supporting the arch of the foot and absorbing shock when walking. If tension and stress on this bowstring become too great, small tears can occur in the fascia. Repeated stretching and tearing can irritate or inflame the fascia. Plantar fasciitis typically causes a stabbing pain in the bottom of your foot near the heel. The pain is usually the worst with the first few steps after awakening, although it can also be triggered by long periods of standing or when you get up after sitting. The pain is usually worse after exercise, not during it.

Turning to FIG. 2, there is shown the anatomy of a human foot F2, showing: the attachment of the hallucis longus 5; the flexor digitorum longus tendons 7; the abductor digiti minimi pedis tendon 9; the flexor hallucis longus 11; plantar aponeurosis (plantar fascia) 3; the abductor hallucis 15; the lateral plantar fascia 17; the tibialis posterior tendon 19; the abductor digiti minimi pedis 21; the flexor digitorum longus tendon 23; the talus 25; and the calcaneus 27.

FIG. 3 is an anatomical illustration of human legs L2 showing the flexor hallucis longus 11. The flexor hallucis longus 11 muscle (FHL) is one of the three deep muscles of the posterior compartment of the leg that attaches (see attachment 5) to the plantar surface of the distal phalanx of the great toe. The other deep muscles are the flexor digitorum longus (7) and tibialis posterior (19); the tibialis posterior (19) is the most powerful of these deep muscles. All three muscles are innervated by the tibial nerve which comprises half of the sciatic nerve.

The plantar fascia (plantar aponeurosis) 3 is a thick layer of fibrous fascia that is located on the plantar surface of the foot and attaches from the tuberosity of the calcaneus 27 proximally to the flexor sheathes of all five toes distally. The plantar fascia 3 functions to stabilize the foot and maintain the arch-structure (supination) of the foot. When the foot is loaded during weight bearing, the arch drops (termed pronation) and the plantar fascia stretches. As the foot is unloaded, the plantar fascia acts like a spring and elastically recoils to reform the arch and supinate the foot. Pronation and supination are natural motions of the foot that occur whenever we walk (the gait cycle) or run.

The plantar fascia 3 is a dense band of connective tissue which extends over the sole of the foot deep in the skin. The plantar fascia originates from the medial tubercle of the calcaneus bone. From there the plantar fascia 3 fans out, covering intrinsic muscles of the foot, blending with the soft tissues of the metacarpophalangeal (MCP) joint complex and continuing as five slips which anchor into the phalangeal bases.

FIG. 1 is a medial side view of the bones of the foot F1 and the plantar fascia 3. As shown, the bones of the foot form a bony arch with the plantar fascia 3 stretched like a bow string between the two ends of the arch. The bony arch is relatively flatter in weight bearing than non-weight bearing positions due to body weight placing soft tissues beneath the arch, including the plantar fascia 3, under increased strain and causing stretching thereof. Placing of the foot in a non-weight bearing position, such as occurs when lying down, reduces the stretch and strain on the plantar fascia 3 and relatively heightens the arch in the foot.

In weight bearing, shortening of the plantar fascia 3 may occur by actively flexing (curling up) the toes, or actively supinating to heighten the arch of the foot. Lengthening of the plantar fascia 3 in weight bearing may occur by actively dorsiflexing the toes, or actively pronating to flatten the arch of the foot. FIG. 1 illustrates the plantar fascia lengthened in weight bearing due to dorsiflexion of the toes.

In individuals having a naturally high arch in weight bearing due to a rigid *cavus* foot, the plantar fascia 3 tends to become shortened and thickened. This is as opposed to individuals with a planus foot type having a naturally flat arch in weight bearing which tends to result in stretching and lengthening of the plantar fascia. Individuals having either a naturally high arch or flat arch in weight bearing may be predisposed to an overuse inflammatory type condition known as 'plantar fasciitis' 1. In this condition the overstressed plantar fascia becomes painful about its attachment to the medial tubercle of the calcaneus. The medial tubercle may be tender to touch, and the tenderness may extend distally along the medial portion of the plantar fascia 3. Plantar fasciitis 1 may occur due to a sudden relative increase in strain and stretch on the plantar fascia 3 such as may occur in individuals who change from non-weight bearing desk job to a weight bearing stand-up job.

For high athletes, plantar fasciitis 1 commonly results from activities such as running or dancing that require dorsiflexion of the metacarpophalangeal joints during plantar flexion of the ankle which stretches the plantar fascia whilst under significant strain.

With reference to FIG. 4, which is an anatomical illustration of human legs L2, a tight plantar fascia can affect the psoas and the quadratus lumborum (QL) since a tight plantar fascia tightens the hamstrings 29 and thus the legs L2 and thereby contributes to back pain and inflexibility. The psoas major contributes to spinal flexion, hip flexion and unilateral side bending of the torso. The quadratus lomborum originates at the iliac crest and the iliolumbar ligament and inserts at the 12th rib and the transverse processes of each lumbar vertebrae. The quadratus lomborum's role is to unilaterally flex the torso (side bend) and elevate the ilium. Bilaterally, it also extends the lumbar spine and fixes the 12th rib during forced expiration. Tightness in the plantar fascia 3 pulls on the talus where the Kelly is also attached acting on the hamstrings 29 causing the lower back to collapse on itself. The hamstrings 29 are notorious for tightening up since they are directly connected to the calves wh ich are tight and to the muscles in the lower back. When the muscles in the hamstrings tighten up, there is pulling on the hips and over time, the lower back becomes sore and irritated as the muscles in the lower back tighten. Once muscles become so tight that they malfunction, other muscles compensate working twice as hard for activities such as standing up straight or swinging a golf ball for example.

Even though plantar fasciitis can develop without an obvious cause, some factors can increase your risk of developing this condition including age, certain types of exercise, foot mechanics, obesity, type of occupation and diabetes. Plantar fasciitis is most common between the ages of 30 and 60. Increasing age, which decreases plantar fascia flexibility and thins the heel's protective fat pad; Activities that place a lot of stress on your heel and attached tissue, such as long-distance running, ballet dancing and aerobic dance, frequent short bursts of physical activity, or spending most of the day on one's feet can contribute to the onset of plantar fasciitis. Flat feet, a high arch or even an abnormal pattern of walking can affect the way weight is distributed when standing and can put added stress on the plantar fascia. Excess pounds put extra stress on your plantar fascia. Factory workers, teachers and others who spend most of their work hours walking or standing on hard surfaces can damage the plantar fascia.

Heel spurs can happen as a reaction to stress, and inflammation caused by plantar fasciitis. Over time the body responds to the stress by building extra bone tissue. This extra tissue becomes a heel spur. Heel spurs occur when calcium deposits build up on the underside of the heel bone, a process that usually occurs over a period of many months. Heel spurs are often caused by strains on foot muscles and ligaments, stretching of the plantar fascia, and repeated tearing of the membrane that covers the heel bone. Heel spurs are especially common among athletes whose activities include large amounts of walking and other activities.

Risk factors for heel spurs include the following: walking gait abnormalities, which place excessive stress on the heel bone, ligaments, and nerves near the heel; running or jogging, especially on uneven or hard surfaces; poorly fitted or badly worn shoes, especially those lacking appropriate arch support; and excess weight.

Heel spurs can be associated with intermittent or chronic pain, especially while walking or jogging if inflammation develops at the point of the spur formation. In general, the cause of the pain is not the heel spur itself, but the soft-tissue injury associated with it. Many people describe the pain of heel spurs and plantar fasciitis as a knife or pin sticking into the bottom of their feet when they first stand up in the morning, a pain that later turns into a dull ache. They often complain that the sharp pain returns after they stand up after sitting for a prolonged period.

Ignoring plantar fasciitis may result in chronic heel pain that hinders regular activities. Changing the way one walks as a way to relieve plantar fasciitis pain might lead to foot, knee, hip or back problems.

Various treatments have been suggested for plantar fasciitis including passive sustained stretching of the calf muscles to reduce tightness. Tightness may reduce an individual's ability to supinate, thereby increasing strain on the plantar fascia. Other treatments include passive sustained stretching of the plantar fascia.

Other foot injuries can occur during golfing for example due to instability during swinging as discussed hereinbelow with reference to FIGS. 5, 6 and 7.

During the golf swing as shown in 5, the body acts as a whip, power production starts with the feet pushing against the ground. The foot pivots and provides intrinsic lateral movement to enable the hip to fully rotate around a fixed leg position. Each foot moves differently during a golf swing, the back foot must allow for more pronation during the follow through of the golf swing than the front foot.

Nevertheless, this motion repeated over an extended period can easily lead to the various golf foot injuries.

Turning to FIG. 6, the sequential movements I, II, and II lateral ankle instability of the forward foot occurs due to the excessive motion of the rearfoot during the golf swing follow through. The forces applied to the lower extremity during the follow through cause an abduction of the knee of the non-dominant limb and a supination of the foot on that side with eversion of the rearfoot. On longer shots, such as a drive, this force can strain the ankle ligaments and peroneal tendons to the point where they cause pain due to the lack of stability cause by biomechanically dysfunctional foot (flat foot or high arch foot) in these cases the fifth metatarsal ray of the foot becomes instable.

Swaying is the swing error that features hips that are moving laterally during the golf swing. During the backswing, hips will slide back towards the back foot and during the downswing and impact, hips will slide forward towards the front foot. In essence, the hips are not staying in place in staying in the box X in FIG. 5. See FIG. 5 for a proper swing is shown in positions C and D where the hips remain in the box X, whereas an improper swing is shown in positions A and B where the hips are outside the box X.

To get to this proper position one need to have rotated their body during the backswing, especially your hips and shoulders. In this way the golfer can control against swaying and make sure they are properly loaded for maximum power in the downswing.

The average cause of the sway motion is the over supination of the foot when it comes from the lower limb instability (i.e the foot) as shown in FIG. 6 movements I to III. Supination (or under-pronation) is the opposite of pronation and refers to the outward roll of the foot during normal motion. A natural amount of supination occurs during the push-off phase of the running gait as the heel lifts off the ground and the forefoot and toes are used to propel the body forward. Over supination can place excessive strain on the ankle and outer toes, causing the ankle to roll or sprain.

An example of over supination is shown in FIG. 8, which shows human legs L3 with the left foot F-L being centered and both the the big toe BT-L and little toe LT-L of the left foot F-L properly positioned on the ground. In contrast, the right foot F-R is shown in an over supination position with the right ankle A-R having rolled away from the centre thereby causing the big toe BT-R of the right foot F-L to be lifted on the ground and turning the right heel H-R towards the centre causing the right foot F-R to roll on its little toe LT-R.

OBJECTS

An object of the present disclosure is to provide an auxiliary inner sole structure for footwear.

An object of the present disclosure is to provide an inner sole structure for being integrated into footwear.

An object of the present disclosure is to provide footwear within an integrated inner sole structure.

An object of the present disclosure is to provide a footwear kit comprising footwear and an inner sole structure therefore.

SUMMARY

In accordance with an aspect of the present disclosure, there is provided an inner sole structure for being mounted to footwear, the footwear comprising a footwear sole defining an outsole for engaging the ground and an inner sole part for supporting a foot of a footwear user, the inner sole structure providing for being mounted on the inner sole part of the footwear to be engaged by the foot, the inner sole structure comprising: a middle sole part comprising top and bottom surfaces thereof defining a middle sole thickness therebetween for providing support to the foot, the middle sole part defining a longitudinal channel devoid of any material therein, extending along a length of the middle sole and defining a longitudinal channel opening at the top surface leading into the longitudinal channel; a top sole part for overlaying the top surface of the middle sole part of the sole thereby covering the longitudinal channel opening at the top surface and defining a longitudinal portion thereof extending along the longitudinal channel opening and the longitudinal channel; wherein when the inner sole structure is mounted to the inner sole part of the footwear and is engaged by the foot, the longitudinal channel under the foot is aligned with a longitudinal portion of the foot corresponding to a plantar fascia position of the foot, wherein the longitudinal portion of the foot engages the longitudinal portion of the top sole part along the longitudinal channel opening and the longitudinal channel thereby avoiding tension to the longitudinal portion of the foot.

In accordance with an aspect of the present disclosure, there is provided a footwear comprising: a footwear sole defining an outsole for engaging the ground and an inner sole part for supporting a foot of a footwear user; an inner sole structure mounted on the inner sole part of the footwear to be engaged by the foot, the inner sole structure comprising: a middle sole part comprising top and bottom surfaces thereof defining a middle sole thickness therebetween for providing support to the foot, the middle sole part defining a longitudinal channel devoid of any material therein, extending along a length of the middle sole and defining a longitudinal channel opening at the top surface leading into the longitudinal channel; a top sole part overlaying the top surface of the middle sole part of the sole thereby covering the longitudinal channel opening at the top surface and defining a longitudinal portion thereof extending along the longitudinal channel opening and the longitudinal channel; wherein when the inner sole is engaged by the foot, the longitudinal channel under the foot is aligned with a longitudinal portion of the foot corresponding to a plantar fascia position of the foot, wherein the longitudinal portion of the foot engages the longitudinal portion of the top sole part along the longitudinal channel opening and the longitudinal channel thereby avoiding tension to the longitudinal portion of the foot.

In accordance with an aspect of the present disclosure, there is provided a footwear kit comprising: a footwear comprising a footwear sole defining an outsole for engaging the ground and an inner sole part for supporting a foot of a footwear user; and an inner sole structure providing for being mounted on the inner sole part of the footwear to be engaged by the foot, the inner sole structure comprising: a middle sole part comprising top and bottom surfaces thereof defining a middle sole thickness therebetween for providing support to the foot, the middle sole part defining a longitudinal channel devoid of any material therein, extending along a length of the middle sole and defining a longitudinal channel opening at the top surface leading into the longitudinal channel; a top sole part for overlaying the top surface of the middle sole part of the sole thereby covering the longitudinal channel opening at the top surface and defining a longitudinal portion thereof extending along the longitudinal channel opening and the longitudinal channel; wherein when the inner sole structure is mounted to the inner sole part of the footwear and is engaged by the foot, the longitudinal channel under the foot is aligned with a longitudinal portion of the foot corresponding to a plantar fascia position of the foot, wherein the longitudinal portion of the foot engages the longitudinal portion of the top sole part along the longitudinal channel opening and the longitudinal channel thereby avoiding tension to the longitudinal portion of the foot.

In an embodiment, the top sole part is mounted to the middle sole part.

In an embodiment, the bottom surface of the middle sole part provides for overlying the inner sole part of the footwear.

In an embodiment, the insole structure further comprises a bottom sole part for being mounted to the bottom surface of the middle sole part.

In an embodiment, the bottom sole part is mounted to the bottom surface of the middle sole.

In an embodiment, the bottom sole part provides for overlying the inner sole part of the footwear.

In an embodiment, the middle sole part comprises an upper body for overlying a separate lower body to provide the middle sole part when combined, the upper body defining the top surface of the middle sole part and the lower body defining the bottom surface of the middle sole part.

In an embodiment, the upper body is more supple and absorbent, and the lower body is more rigid.

In accordance with an aspect of the present disclosure, there is provided an inner sole structure for being mounted to footwear, the footwear comprising a footwear sole defining an outsole for engaging the ground and an inner sole part for supporting a foot of a footwear user, the inner sole structure comprising: a support element for being mounted to the inner sole part of the footwear to be engaged by the foot, wherein when the support member is mounted to the inner sole part of the footwear and is positioned to be engaged by a region of the foot corresponding to a position extending between at least near a fifth metatarsal rear end position of the foot to a heel bone position of the foot for providing stability to the foot for controlled supination.

In accordance with an aspect of the present disclosure, there is provided a footwear comprising: a footwear sole defining an outsole for engaging the ground and an inner sole part for supporting a foot of a footwear user; and an inner sole structure comprising a support element mounted to the inner sole part of the footwear to be engaged by the foot, the support member being positioned to be engaged by a region of the foot corresponding to a position extending between at least near a fifth metatarsal rear end position of the foot to a heel bone position of the foot for providing stability to the foot for controlled supination.

In accordance with an aspect of the present disclosure, there is provided a footwear kit comprising: a footwear comprising a footwear sole defining an outsole for engaging the ground and an inner sole part for supporting a foot of a footwear user; and an inner sole structure comprising a support element for being mounted to the inner sole part of the footwear to be engaged by the foot, wherein when the support member is mounted to the inner sole part of the footwear and is positioned to be engaged by a region of the foot corresponding to a position extending between at least near a fifth metatarsal rear end position of the foot to a heel bone position of the foot for providing stability to the foot for controlled supination.

In an embodiment, the at least near a fifth metatarsal rear end position is at or behind the rear end of the fifth metatarsal.

In an embodiment, the heel bone position is at or behind a front end of the heel bone.

In an embodiment, the support element is positioned beneath a top surface of the inner sole part of the footwear directly engaged by the foot pushing this top surface upwardly against the foot when engaged thereby.

In an embodiment, the inner sole structure further comprising a top sole part having a top surface and an undersurface with the support element mounted thereto, the top sole part providing for being mounted to a top surface of the inner sole part of the footwear with the support element resting thereon.

In an embodiment, the support element comprises a bar. In an embodiment, the bar comprises a rectangular configuration.

Other objects, advantages and features of the present disclosure will become more apparent upon reading of the following non-restrictive description of illustrative embodiments thereof, given by way of example only with reference to the accompanying drawings.

DETAILED DESCRIPTION OF ILLUSTRATIVE EMBODIMENTS

Figure 1:
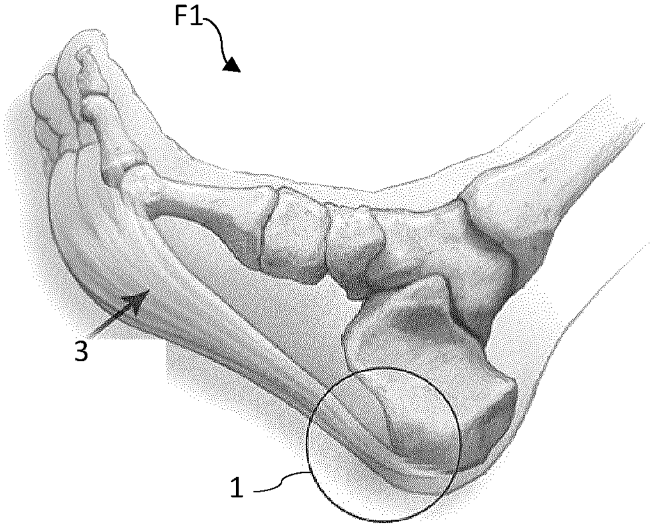
FIG. 1 is a lateral side view illustration of the anatomy of the human foot.

Generally stated, there is provided an inner sole structure for being mounted to footwear. The footwear comprising a footwear sole defining an outsole for engaging the ground and an inner sole part for supporting a foot of a footwear user. The inner sole structure provides for being mounted on the inner sole part of the footwear to be engaged by the foot. The inner sole structure comprises a middle sole part comprising top and bottom surfaces thereof defining a middle sole thickness therebetween for providing support to the foot. The middle sole part defines a longitudinal channel devoid of any material therein that extends along a length of the middle sole and defines a longitudinal channel opening at the top surface leading into the longitudinal channel. A top sole part overlies the top surface of the middle sole part of the sole thereby covering the longitudinal channel opening at the top surface and defining a longitudinal portion thereof extending along the longitudinal channel opening and the longitudinal channel. When the inner sole structure is mounted to the inner sole part of the footwear and is engaged by the foot, the longitudinal channel under the foot is aligned with a longitudinal portion of the foot corresponding to a plantar fascia position of the foot. The longitudinal portion of the foot engages the longitudinal portion of the top sole part along the longitudinal channel opening and the longitudinal channel thereby avoiding tension to the longitudinal portion of the foot.

The present disclosure provides an inner sole structure that is either auxiliary to footwear and so can be removably positioned therein or integrated into the footwear. Thus, the present disclosure also provides footwear comprising the inner sole structure. Footwear includes, without limitation, shoes, slippers, sandals, boots, orthosis and the like as is understood in the art. An inner sole structure includes a portion or portions of the sole opposite the outer sole i.e., the part of the sole that is positioned beneath the foot for synergistically supporting the foot within the footwear and not for engaging the ground surface. In an embodiment the inner sole structure includes the insole and/or the midsole and or portions thereof as will be readily understood by the skilled artisan within the context of the present disclosure.

In an embodiment, the inner sole structure of the present disclosure provides relief of plantar fasciitis as well as the tendon *flexus* hallucis longus and the heel spur.

In an embodiment, the inner sole structure of the present disclosure provides for liberating the tension of the plantar fascia (plantar aponeurosis) and the tendon *flexus* hallucis longus.

In an embodiment, the inner sole structure of the present disclosure provides a longitudinal channel positioned under the area of the foot corresponding to the plantar fascia for releasing the tension under the plantar fascia and the heel while supporting the arch of the foot.

In an embodiment the channel described herein releases the fasciitis under the heel and the spur. In an embodiment, the term "releasing the fasciitis" comprises prevention of pressuring the fascia in movements of the foot what will invariably occur. Therefore, releasing the tension on the fasciitis with the channel positioned thereunder further means that flexing the foot will not be stressing the plantar fascia while standing or walking or running.

In an embodiment, the inner sole structure of the present disclosure provides for the plantar fascia and/or or the heel spur to decompress so it can relax while the rest of the foot is being supported about the channel allowing plantar fascia to heal since the area of the foot sole corresponding to the position of the plantar fascia is not engaging any material but rather "hanging" within the channel and this is not under any tension or pressure.

In an embodiment, the inner sole structure of the present disclosure provide for the wearer's foot to have better ankle motion providing for ankle dorsiflexion or stretching of the ankle plantar flexor muscles. Increasing ankle dorsiflexion is desired to maintain normal gait. When having fasciitis or heel spurs reduced motion or reduced dorsiflexion causes limping.

In an embodiment, the inner sole structure of the present disclosure reduces or removes foot pain by releasing foot tension under the plantar fascia and under the heel with a channel.

With reference to FIGS. 8-13, non-restrictive illustrative embodiments will be described to further exemplify the disclosure only and by no means limit the scope thereof.

Figure 8:
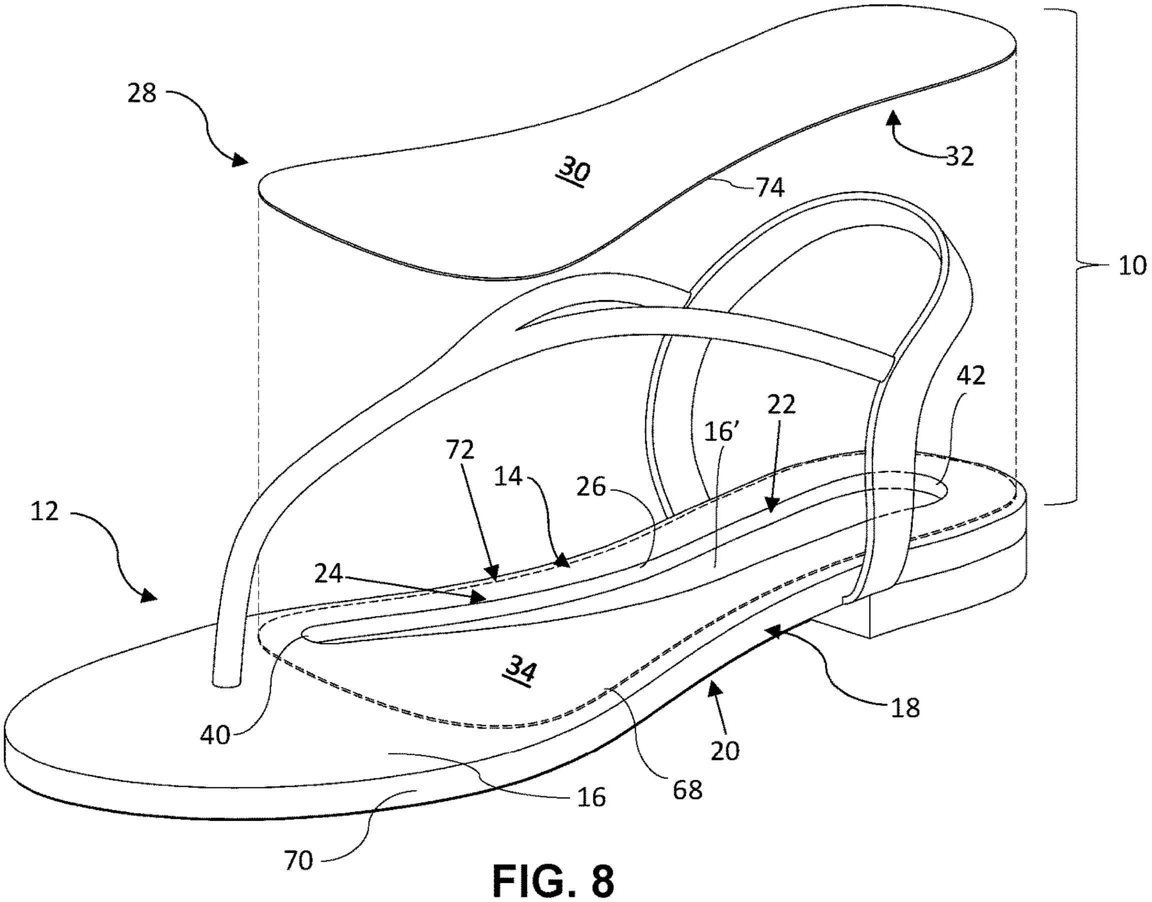
FIG. 8 is an exploded perspective view of an inner sole structure for footwear in accordance with a non-limiting illustrative embodiment of the present disclosure.

With reference to FIG. 8 there is shown in inner sole structure 10 integrated within a footwear 12 such as a sandal for example but the description of inner sole structure is applicable to any type of footwear as provided herein.

In an embodiment, the inner sole structure 10 comprises an inner sole body 14 that is directly mounted to the upper surface 16 of the bottom sole 18 of the footwear 12 defining an outer sole undersurface 20 for engaging the ground. The inner sole body 14 has a thickness and therefor upwardly extends from the upper surface 16 of the bottom sole 18. The inner sole body 14 defines a longitudinal channel 22 that provides a longitudinal opening 24 exposing a portion 16' of the upper surface 16 therethrough. The thickness of the inner sole body 14 defines an inner wall 26 of the channel 22 which defines the depth Δ (see FIG. 13) of the inner channel 22. The inner sole structure 10 comprises an insole 28 for being mounted on the inner sole body 14 (which in this example acts as a midsole) and thus covering the channel 22. The wearer can thus place their foot on the top surface 30 of the insole 28 with the undersurface 32 thereof mounted to the top surface 34 of the midsole (or inner sole body) 14. The foregoing arrangement is better shown in FIG. 13.

Figure 13:
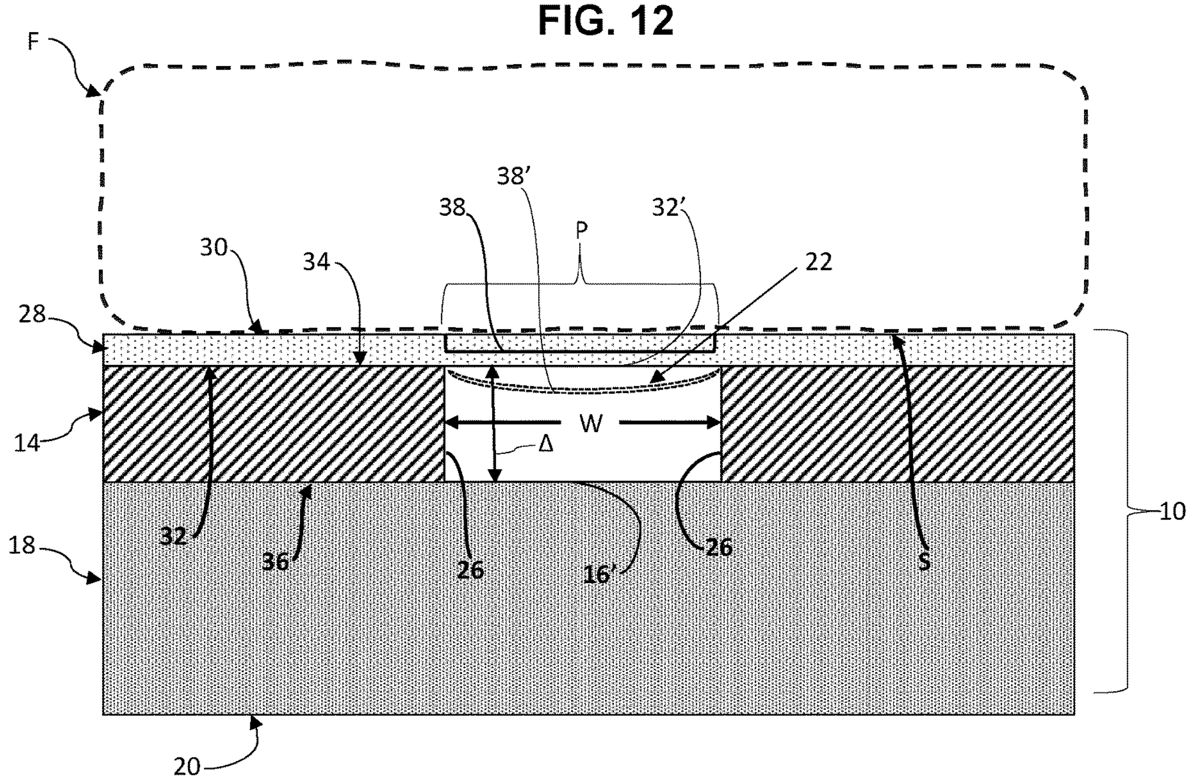
FIG. 13 is a cross sectional schematic representation of an inner sole structure for footwear in accordance with a non-limiting illustrative embodiment of the present disclosure.

Turning to Figure to FIG. 13, the inner sole structure 10 is shown comprising a middle part such as the the midsole 14 sandwiched between a top part such as the insole 28 at the upper/top side 34 of the midsole 14 and a bottom part such as the bottom sole 18 at the underside 36 of the midsole 14. The midsole 14 defines the channel 22 which is devoid of any space therein but is closed at the top by the insole 28 and at the bottom by the bottom sole 18.

Figure 10:
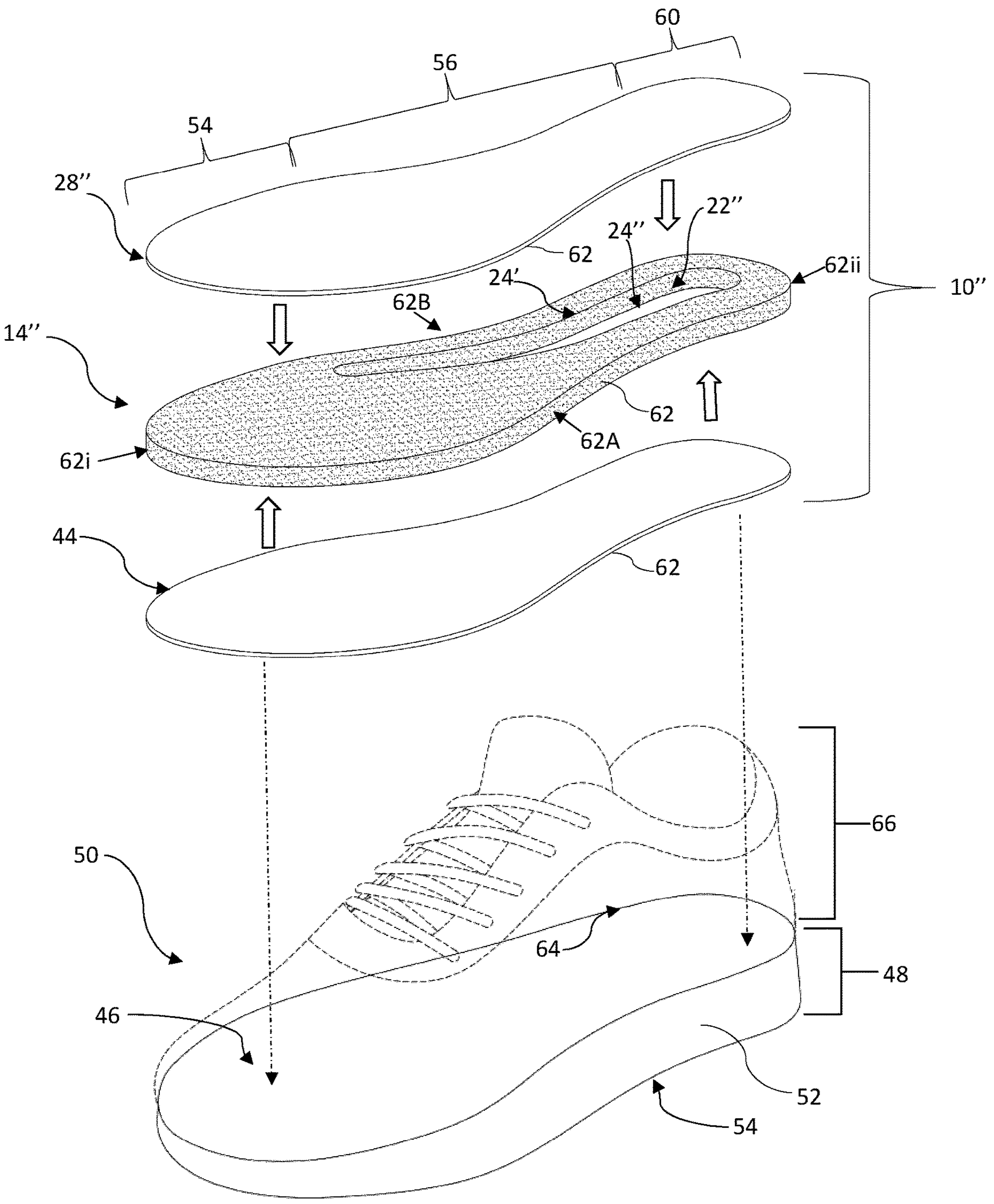
FIG. 10 is an exploded perspective view of inner sole structure for footwear in accordance with another non-limiting illustrative embodiment of the present disclosure.

Therefore, the channel 22 provides a longitudinal channel opening 24 at the top surface 34 of the middle part 14 and at the bottom surface 36 of the middle part as better shown in the example of middle part 14" in FIG. 10 (see top and bottom longitudinal openings 24' and 24").

The depth Δ of the channel 22 is delimited at the top by the undersurface portion 32' of the insole 28 and the top surface portion 16' of the bottom sole 18. The foot F of the footwear 12 wearer engages the top surface 30 of the insole 28 and rests thereon being supported by the insole 28 and the midsole 14 with a portion P of the sole S or the foot F being aligned with the channel 22 resting on a portion 38 of the insole 28 that is aligned with the channel 22 and thus there is no support thereunder due to the empty space defined by the channel 22 thereby avoiding any tension on portion P of the foot F. The portion 38 is a longitudinal portion that extends along the length of the longitudinal channel opening 24 at the top surface 34 and the longitudinal channel 22. Portion P of the sole S of the foot F is the area of the foot that corresponds to the plantar fascia. Indeed, channel 22 has been configured to align with the longitudinal portion P of sole of the foot that corresponds with the position of plantar fascia along the sole. The foregoing arrangement is better shown in FIG. 9.

Figure 2:
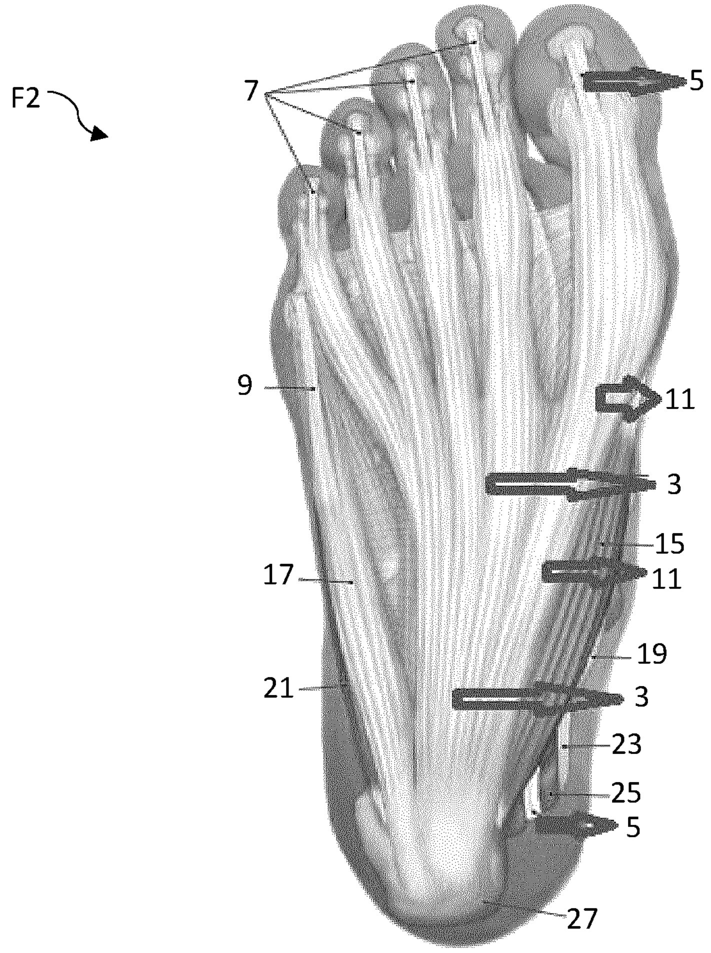
FIG. 2 is bottom view illustration of the anatomy of the human foot.
Figure 3:
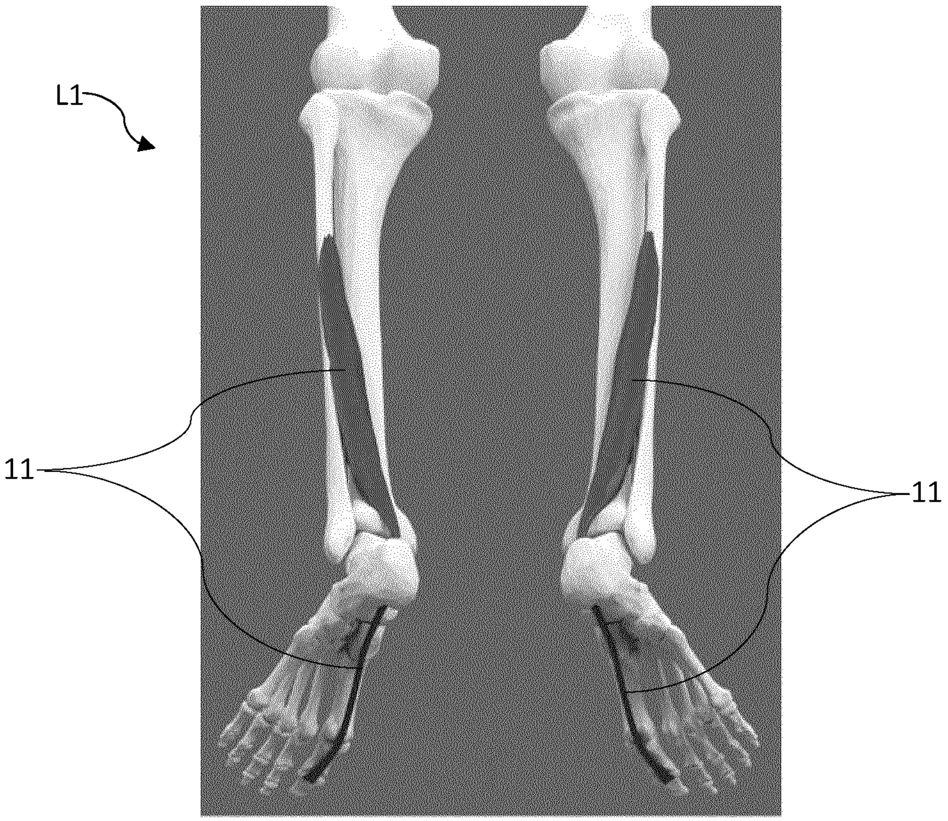
FIG. 3 is a rear view illustration of the anatomy of human legs.
Figure 4:
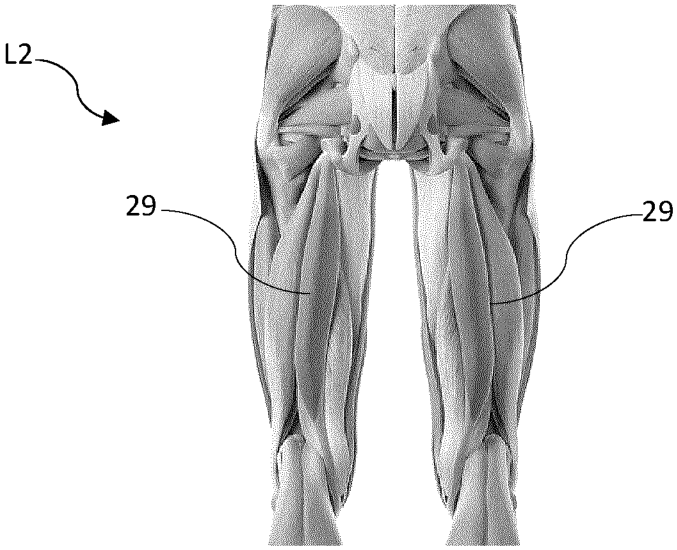
FIG. 4 is another rear view illustration of the anatomy of human legs.
Figure 5:
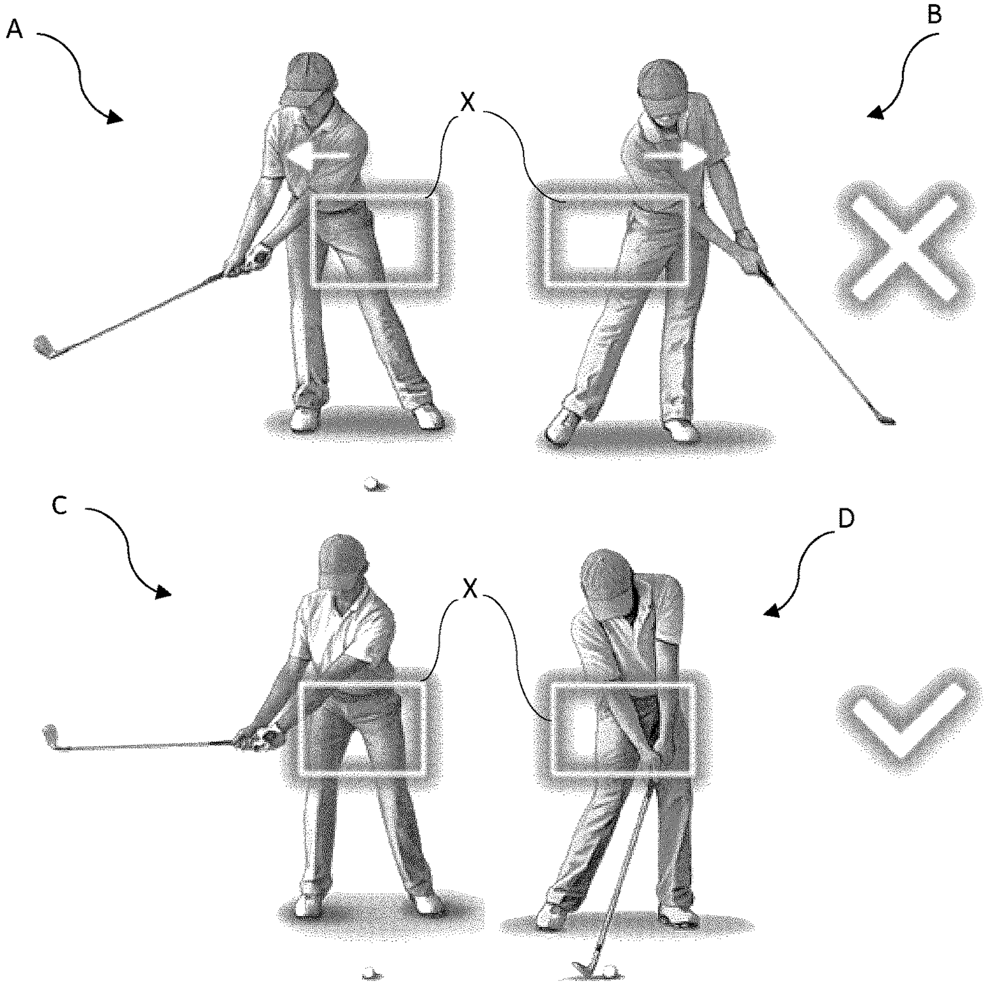
FIG. 5 is an illustration of proper and improper movements for golfing.
Figure 6:
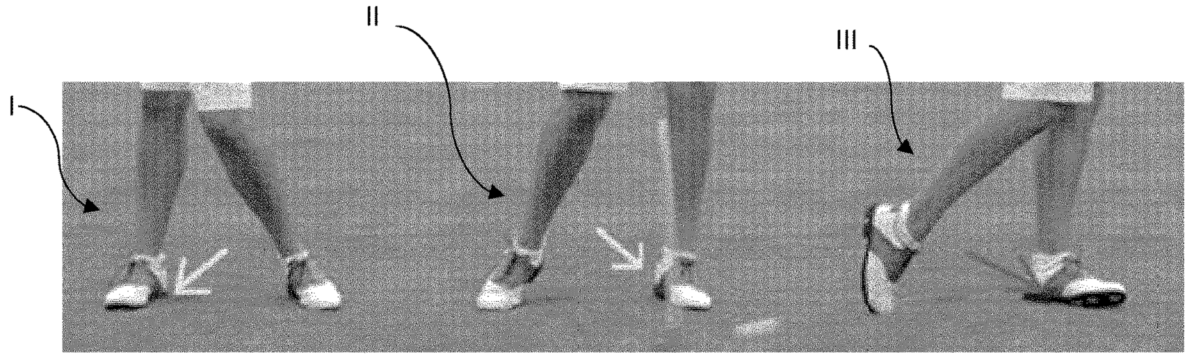
FIG. 6 is a photo of time stamp foot movement positions during golfing.
Figure 9:
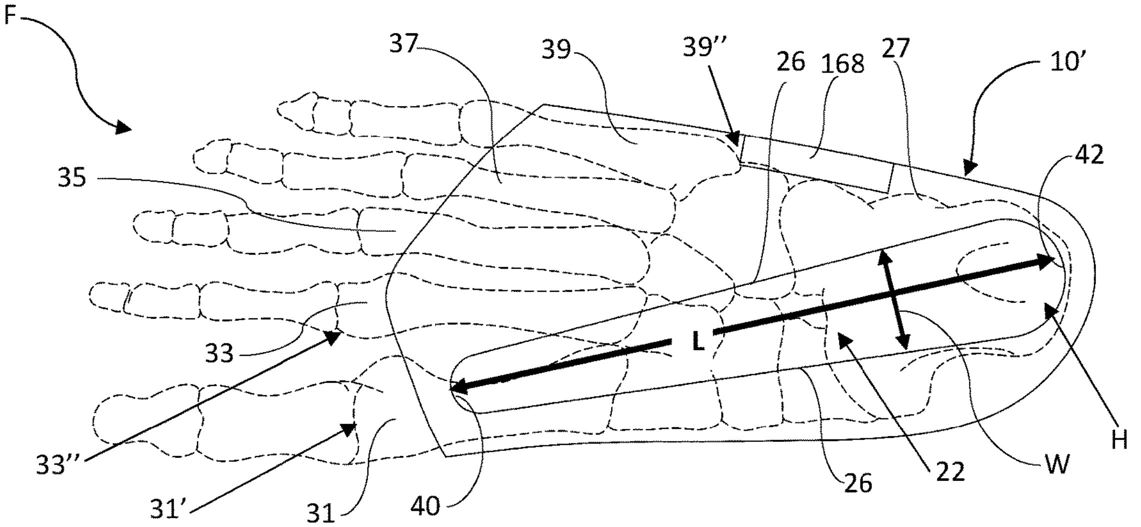
FIG. 9 is a bottom plan schematic view of an inner sole structure in accordance with a non-limiting illustrative embodiment of the present disclosure and superimposed on foot skeleton for reference.

Turning to FIG. 9 and with reference to FIG. 2, the channel 22 is positioned to be aligned with the plantar fascia of the human foot F wearing the footwear. FIG. 9 shows the anatomy of a sole of a foot positioned on the insole structure 10' that includes the channel 22. The foot F is shown having first, second, third, fourth and fifth metatarsals, denoted with reference numerals 31, 33, 35, 37 and 39 respectively. In an embodiment, the front end 40 of the channel 22 (see also FIG. 8) begins at the region of the first and second metatarsals 31 and 33 respectively. The rear end 42 is positioned behind the talus 25 at the region of the calcaneus 27 (the heel bone). The channel 22 thus runs along the plantar fascia 3 (shown in FIG. 2). The length L of the channel 22 is defined between the front end 40 and the rear end 42. The length L is determined on the basis of the footwear size. In an embodiment, the channel 22 runs from the ball of the foot or the end of the ball along the arch of the foot towards the heel H of the foot F. Thus, the channel 22 is configured to substantially follow the pathway of plantar fascia 3 along the sole S of the foot F.

The depth Δ of the channel 22 corresponds to the thickness of middle part 14 defined between its upper/top surface side 34 and underside/bottom surface 36 and this thickness conveniently provides support and comfort to the foot F. The top part 28 is a thin layer of material acting like a cover to the middle part 18 and acts as an insole. Therefore, there is no tension to the aforementioned area of the sole corresponding to plantar fascia 3 of the foot F when portion P of the foot F engages portion 38 of the top part 28.

In an embodiment, the channel 22 has a front end 40 that starts behind the front ends 31', 33', respectively, of the first and second metatarsals 31 and 33 running along the arch as it follows the pathway of the plantar fascia and continues under the heel H (see FIG. 9) at the calcaneus 27 behind the talus 25. In an embodiment the front end 40 starts about 1 mm starts behind the front ends 31', 33', respectively, of the first and second metatarsals 31 and 33.

In an embodiment, the depth Δ (see FIG. 13) of the channel 22 is from about 4 mm to about 12 mm deep (and as such the thickness of the middle part 14 is from about 4 mm to about 12 mm deep).

In an embodiment, the width W (see FIGS. 9 and 13) is defined between the interfacing inner walls 26 is from about from 12 mm to about 24 mm. In an embodiment the channel has a constant width W along its length L. In an embodiment the width in the area of the channel 22 near and at the front end 40 is lesser than the width of the area of the channel near and at the rear end 42. In an embodiment the foregoing rear end area is twice the width of the foregoing front end area. In an embodiment, the width W increases along the length L of the channel 22 from the front end 40 thereof towards the rear end 42 thereof. In an embodiment, the front end area width is about 12 mm and the rear end area width is about 24 mm.

Turning now to FIG. 10, there is shown an inner sole structure comprising a middle part 14' that is similar to midsole 14 described above and as such only the differences therewith will be described for concision purposes only. Indeed, the middle part 14" is a full inner sole body with a front section for receiving the full ball and toes of the sole S of the foot F.

The middle part 14 defines a channel 22" which is similar to channel 22 described above and thus does not require further discussion. The middle part 14" receives a top part 28" thereon. Top part 28" is similar to the insole 28 described above and as such only the differences therewith will be described for concision purposes only. Like the middle part 14", the top part 28" is a full sole body with a front section for receiving the full ball and toes of the foot. The middle part 14" receives a bottom part 44 thereunder such that the middle part 14" is sandwiched between the top part 28" and the bottom part 44 much like the middle part 14 is sandwiched between the top part 28 and bottom part 18 as shown in FIG. 13 and as described above. Therefore, the description of the bottom part 18 in FIG. 13 is applicable to bottom part 44 except that bottom part 44 does not define an outsole. Therefore, the descriptions for FIGS. 9 and 13 are applicable to the embodiment shown in FIG. 10 mutatis mutandis.

In an embodiment, the bottom part 44 is similar to the top part 28". In an embodiment the bottom part 44 can be thinner or thicker with lesser or higher density than the top part 28".

In an embodiment, the inner sole structure 10" is provided in a singe piece of three integrated parts 28", 14" and 44. As such, the inner sole structure 10" forms an auxiliary inner sole structure that is removably positioned on the insole 46 of the sole 48 of a footwear 50 such as a running shoe for example. The inner sole structure 10" functions in the same way as insole structure 10 and 10' described above function.

The sole comprises a bottom sole part 52 defining the outsole 54 and the bottom part 44 and the bottom sole part 52 of sole 48 correspond to a bottom part 18 in FIG. 13.

The inner sole structure 10" when assembled has a front section 56 for receiving the ball and toes of the foot F, a middle section 58 for receiving the arch of the foot F and a rear section 60 for receiving the heel H of the foot F.

The inner sole structure 10" when assembled defines a common perimeter 62 as its parts described herein are similarly sized. As illustrated in the example of FIG. 10, parts 28", 14" and 44 are correspondingly configured so as to have their respective perimeters being aligned. The perimeter 62 defines the front and rear ends 62*i* and 62*ii*, respectively and the lateral sides, 62A and 62B of the sole structure 10" and each of the respective parts 28", 14" and 44. This common perimeter engages or interfaces with the inner wall 64 of the upper body 66 of the footwear 50 extending from the sole 48. This inner wall is directly above the insole 46 and circumscribes the area where the foot F contacts the insole 46 as can be readily understood by the skilled artisan.

In an embodiment, the inner sole structure 10" comprises only the middle part 14" with the top part 28" mounted thereon as a cover and as previously explained but does not include the bottom part 44. In the foregoing embodiment of the inner sole structure 10", the auxiliary inner sole structure 10" is removably positioned on the inner sole 46 (of the bottom sole 48) which acts as the bottom part 44 thereof.

In an embodiment, the inner sole structure 10" comprises parts 28", 14" with or without par 44 yet, the foregoing parts are not integrated into a single piece, but three separate pieces that are positioned on the insole 46 as discussed hereinabove.

In an embodiment, the insole 46 is removed (the insole 46 is configured much like the top part 28" or insole 28) and the middle part 14" is placed thereunder and sandwiched between the insole 46 and the bottom sole 52 defining the outsole 54. In this embodiment, the middle part 14" acts as a midsole. In an embodiment, the middle part 14" is an integrated part of the footwear 50.

Turning back to FIG. 2, the middle part 14 defines a perimeter 68 thereof that is inward relative to the perimeter 70 of the bottom part 18. In an embodiment, the bottom part 18 is comprises a cavity 72 corresponding to the size and depth of the middle part 14 for nesting the middle part 14 therein. In an embodiment, the perimeter 74 of the top part 28 may be aligned or not with the perimeter 70.

Figure 11:
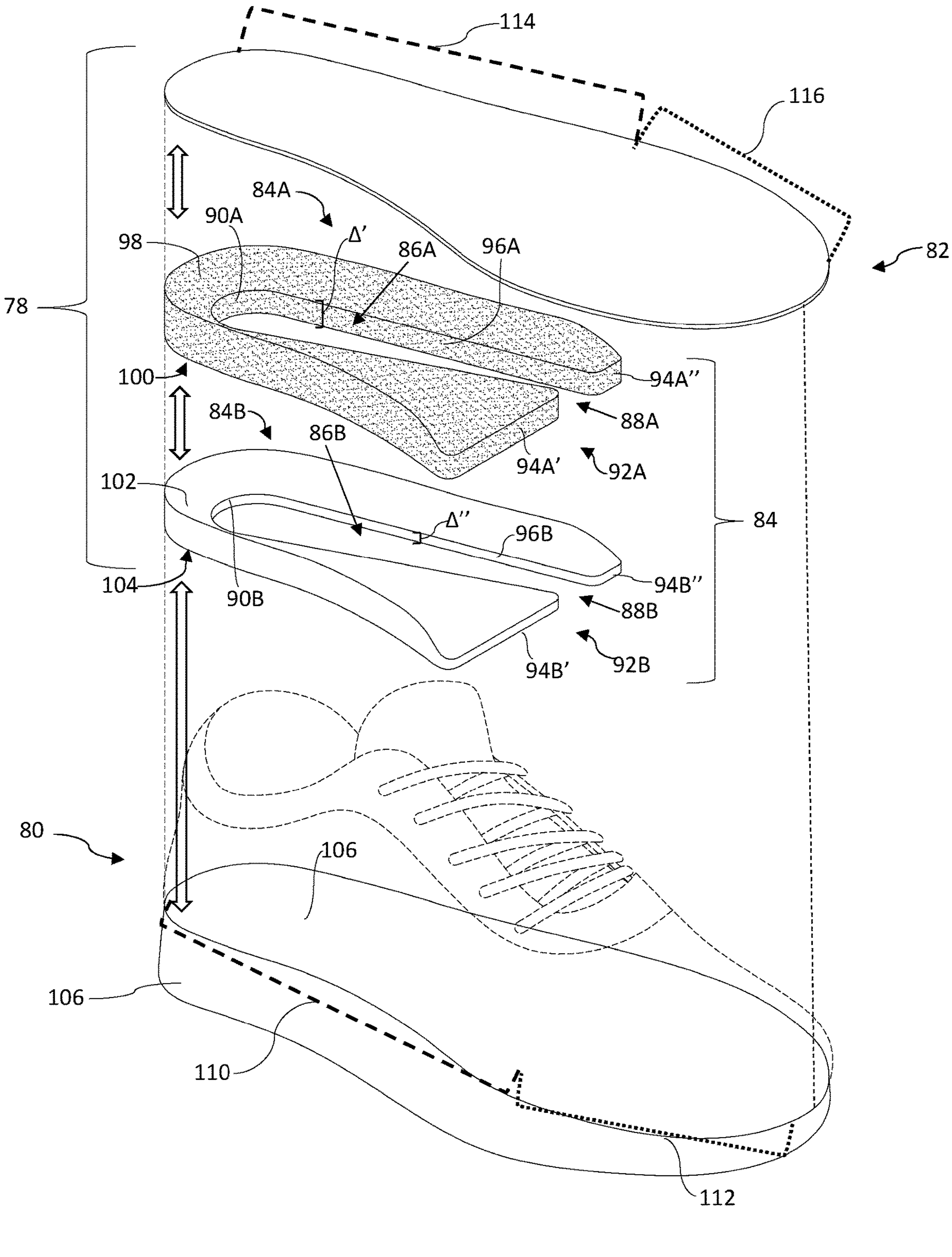
FIG. 11 is an exploded perspective view of inner sole structure for footwear in accordance with a further non-limiting illustrative embodiment of the present disclosure.

Turning now to FIG. 11, there is shown an inner sole structure 78 for a footwear 80 such as an athletic shoe for example.

The insole structure 78 comprises a top part such as insole 82 for being engaged by the foot F as previously explained and thus top part 82 is similar to top parts 28 and 28" previously described. Indeed, top part 82 is a full sole body much like top part 28".

The inner sole structure 78 comprises a middle part 84 that is formed of two separate middle part bodies 84A and 84B. Bodies 84A and 84B are correspondingly configured and assembled with body 84A being layered on body 84B to provide the assembled middle part 84. As such, the middle part 84 comprises an upper body 84A and a lower body 84B.

In an embodiment, the upper body 84A is formed of a more supple material to provide comfort, absorption, and support to the foot F. In an embodiment, the lower body 84B is formed of a more rigid material to provide support and stability to the upper body 84A layered thereon. In an embodiment, the upper body 84A is thicker than the lower body 84B. Of course, the thickness of the middle part 84 is defined by the combined thickness of both bodies 84A and 84B.

The middle part 84 when assembled is similarly configured to middle part 14" except that it is truncated relative to middle part 14" as will be further explained herein.

The upper body 84A defines an upper channel 86A that is similarly configured to channel 22 except that it has an open upper front end 88A (rather than a closed front end 40) yet includes a closed upper rear end 90A (like end 42). Upper channel 86A, like channel 22 shown in FIG. 9, is aligned with the portion P (see FIG. 13) of the sole S the foot F that corresponds to plantar fascia 3 (see FIG. 2). The upper front end 92A of the upper body 84A forms two separate straight upper front sections 94A' and 94A" with the open upper channel front end 88A interposed therebetween. The thickness of the upper body 84A defines an inner upper channel wall 86A that like wall 26 defines the depth Δ' of the upper channel 86A. The top surface 98 of the upper body 84A receives the top part 82 thereon which covers the upper channel 86A. The underside 100 of the upper body 84A overlies the lower body 84B.

The lower body 84B defines a lower channel 86B that is similarly configured to channel 22 except that it has an open lower front end 88B (rather than a closed front end 40) yet includes a closed lower rear end 90B (like end 42). Lower channel 86B, like channel 22 shown in FIG. 9, is aligned with the portion P (see FIG. 13) of the sole S the foot F that corresponds to plantar fascia 3 (see FIG. 2). The lower front end 92B of the lower body 84B forms two separate straight upper front sections 94B' and 94B" with the open lower channel front end 88B interposed therebetween. The thickness of the lower body 84B defines an inner lower channel wall 96B that like wall 26 defines the depth Δ" of the lower channel 86A. The top surface 102 of the lower body 84AB receives the undersurface 98 of the upper body 84A for aligned assembly therewith to define the middle part 84. The underside 104 of the lower body 84A overlies the top surface 106 of the bottom sole 108 of the footwear 80.

Indeed, when the middle part 84 is assembled, the upper channel 86A and the lower channel 86B are aligned to form a single channel that has a single common front end (provided by the alignment of 88A and 88B) and a single common rear end (provided by the alignment of 90A and 90B) and that has a single depth (the combination of Δ' and Δ") similar to that described for middle part 14 and a configuration as shown in FIG. 9 for channel 22.

As the middle part 84 is truncated it will have a shape somewhat similar to structure 10' shown in FIG. 9 yet with a straight line running through the structure 10' aligned with front end 40 thereof. As such, the middle part 84 covers a mid to rear section 110 of the top surface 106 of the bottom sole 108 leaving a front section 112 thereof unengaged by the middle part 84. Similarly, only the mid to rear section 114 of the top part 82 overlies the middle part 84 leaving a front section 116 thereof that does not overly the middle part 84. As such, when the structure 78 is assembled to or integrated with the footwear 80, the front section 116 of the top part overlies the front section 112 of the top surface 106 of the bottom sole 108. In an embodiment, additional material is added between overlying section 116 and 112.

Therefor, the middle part 84 together with the top part 82 provide for upwardly supporting the foot at section 116 all the while leaving a portion of the top part 84 such as portion 38 in FIG. 13 without any material thereunder (like channel 22 in FIG. 13) so that there is no tension under portion P of the foot F which corresponds to the position of the plantar fascia 3 (see FIGS. 2 and 9).

The inner sole structure 78 can be integrated to the footwear 80 or auxiliary thereto for being mounted to the footwear 80 by assembling the parts thereof as shown herein.

Figure 12:
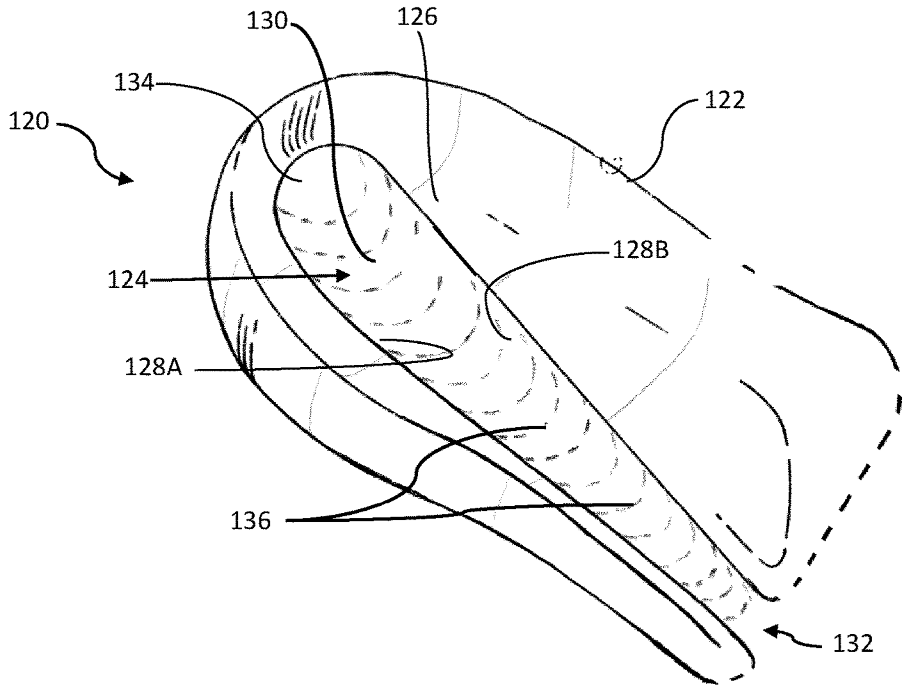
FIG. 12 is a perspective view of inner sole structure for footwear in accordance with yet another non-limiting illustrative embodiment of the present disclosure.

With reference to FIG. 12, there is shown an inner sole structure 120 comprising a bottom sole portion 122 that is molded within footwear including a channel 124 so positioned as to be aligned with the part P of the sole S of the foot corresponding to the plantar fascia. In this example, the channel 124 is concave cylindrical like groove dug into the top surface 126 of the bottom sole portion 122. The channel 124 is covered by a top part such as an insole as previously described. The channel 124 is defined by side curved walls 128A and 128B which meet at a curved bottom floor 130. The channel 132 has front end 132 which can be open and a closed rear end 134. The channel 132 may be tapered with the front portion thereof having a smaller width than the rear portion thereof as shown in FIG. 12. Thus, providing a configuration that generally corresponds to channel 22 in FIG. 9. In a embodiment, circular ridges 136 extend along the side walls 128A and 128B via the bottom floor 130 therebetween providing semi-ring or rib like structures which provide stability to the material forming the concave cylindrical groove 124. In an embodiment, the concave groove 124 is molded in the shape of the fascia which is round thereby accommodating this shape.

It should be noted that for all inner sole structures provided herein, the portion 38 in FIG. 13 of the top part which lies above the channel 22 may bend inwardly as indicated by 38' thereby providing no tension at all to the portion P of the sole S of the foot. The portion P only feels material 38 but this material is loose and free moving along with the skin without any counter force.

The undersurface of any of the inner sole structures provided herein that engages the structural inner surface of footwear may be provided with adhesive material for adhesively connecting thereto.

In an embodiment, the channels of the inner sole structures herein accommodate the shape of the fascia and provide for releasing the tension of the fascia as the user walks or runs.

In an embodiment, the inner sole structures herein can be integrated in a moldable material in an insole or footwear.

In an embodiment, the inner sole structures herein can be integrated within footwear by layering one or more layers of material to create the channel.

In an embodiment, the inner sole structure of at least the part thereof defining the channel can be made for example and without limitation thereto from rubber, epoxy polymer, carbon fibers, liege, Vibram and other moldable types of convenient material and combinations thereof.

The plantar fascia is a thick band of connective tissue that runs along the underside of the foot, from the heel bone to the metatarsals. Its function is to support the arch of the foot by carrying tension when the foot bears weight. By providing an empty channel right under the plantar fascia, this creates a soft spot within the insole that relaxes the plantar fascia and thus avoids pain to the wearer and injury.

Generally stated and in accordance with an aspect of the present disclosure, there is provided an inner sole structure for being mounted to footwear. The footwear comprises a footwear sole defining an outsole for engaging the ground and an inner sole part for supporting a foot of a footwear user. The inner sole structure comprises a support element for being mounted to the inner sole part of the footwear to be engaged by the foot. When the support member is mounted to the inner sole part of the footwear it is positioned to be engaged by a region of the foot corresponding to a position extending between at least near a fifth metatarsal rear end position of the foot to a heel bone position of the foot for providing stability to the foot for controlled supination.

With reference to FIGS. 9, and 14-18, non-restrictive illustrative embodiments will be described to further exemplify the disclosure only and by no means limit the scope thereof.

Figure 14:
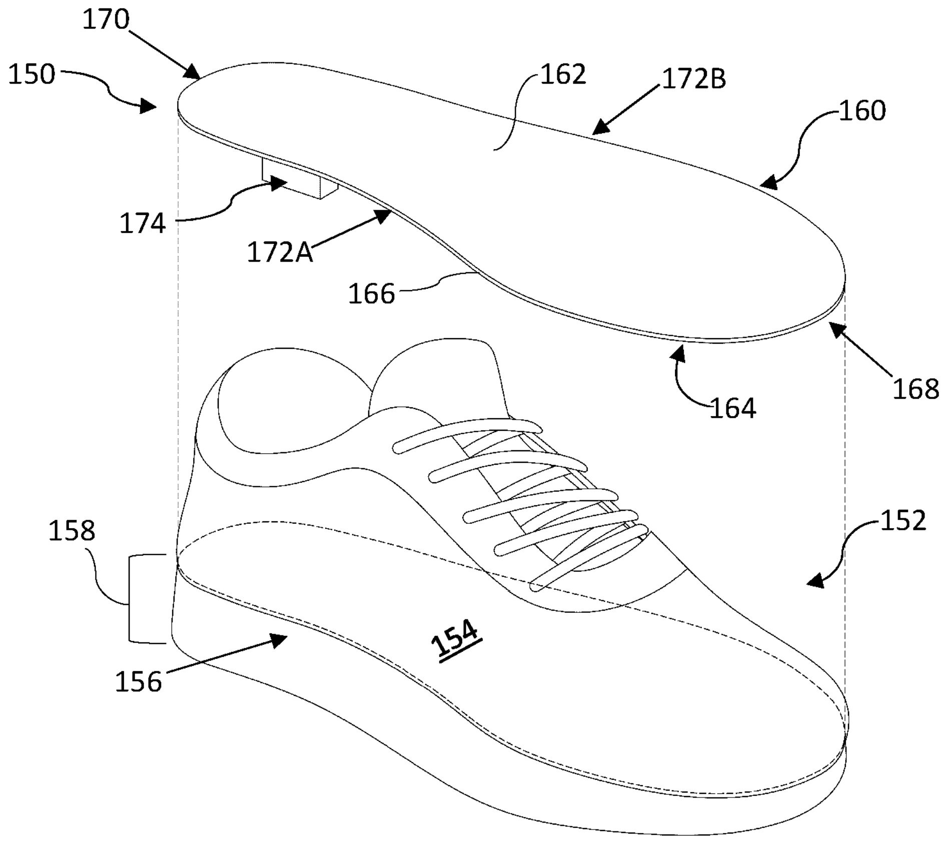
FIG. 14 is a perspective view of an inner sole structure for being mounted to footwear in accordance with a non-limiting illustrative embodiment of the present disclosure.
Figure 15:
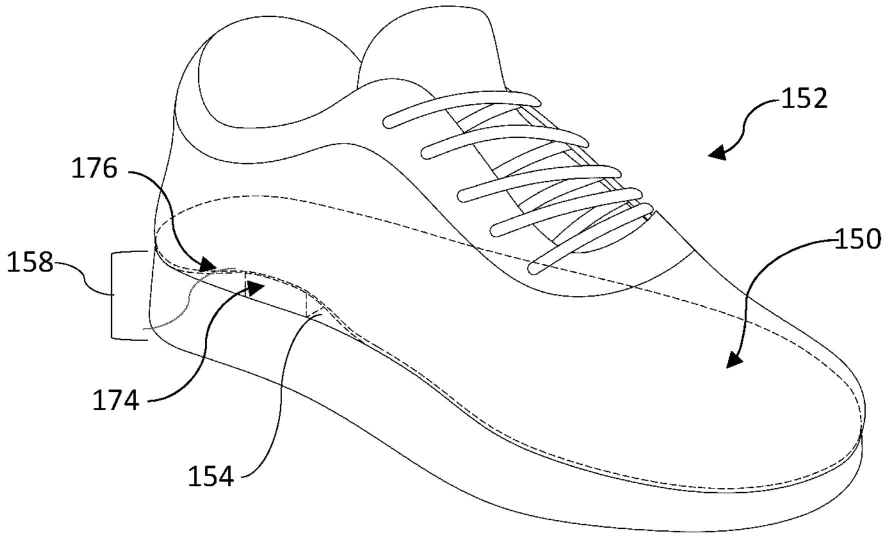
FIG. 15 is a perspective view of the inner sole structure of FIG. 14 mounted to the footwear in accordance with a non-limiting illustrative embodiment of the present disclosure.

With reference to FIGS. 14 and 15, there is shown an auxiliary inner sole structure 150 for being positioned within footwear, such as shoe 152 to overly the top surface 154 of the footwear inner sole part 156 of the sole 158.

The inner sole structure 150 comprises a main sole body 160 defining a top surface 162, an undersurface 164 and a perimeter 166 therebetween. The perimeter 166 defines the front and rear ends, 168 and 170, respectively of the body 160 as well as the lateral sides 172A and 172B of the body 160.

A support element in the form of a bar 174 is positioned on the undersurface 164 of body 160 towards the lateral side 172A and at least near the rear end 170. The inner sole structure 150 is positioned on the top sole surface 154 of the footwear 152 with the support rested thereon as well and keeping a portion 176 of the undersurface 164 spaced from the footwear to sole surface 154. When the foot F engages the inner sole structure 150 the support bar 174 is pushed into the sole 158 which is resilient and thereby causes an opposite upward resistance to the support bar 174 pushing into the region of the foot F that overlies the support bar 174.

Figure 18:
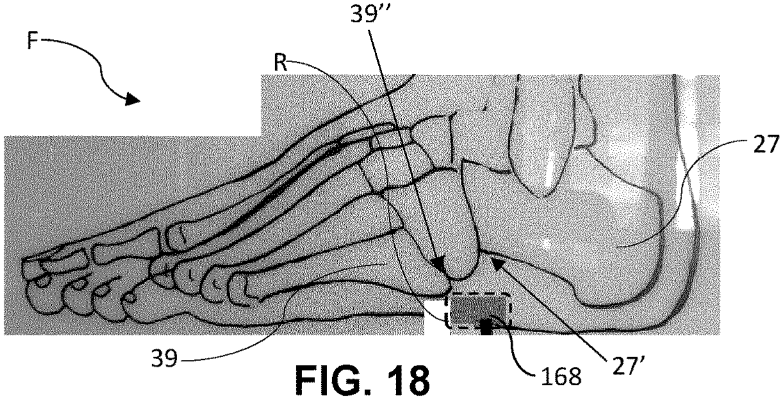
FIG. 18 is a schematic representation of the support element of the inner sole structures of FIGS. 14 to 16 superimposed on a foot skeleton for reference in accordance with an illustrative embodiment of the present disclosure.

Turning to FIG. 18, the support element 174 is so positioned as to engagingly interface with the side region R of the foot F corresponding to the area from about or near (including just behind) the end 39" of the fifth metatarsal 39 to about or near the beginning 27' of the heel bone (calcaneus 27).

In an embodiment shown in FIG. 9, the support element 174 is positioned to engagingly interface with the region R of the sole S of foot F corresponding to the area right behind the fifth metatarsal 39 which ends at 39" and runs along until a front portion of the heel bone (calcaneus 27).

As previously discussed, a golf swing, the outside of each ankle constantly gets turned over into the ground i.e. supinates which leads to swaying. Thus, the support element 174 stabilises the fifth metatarsal to provide stability to the ankle preventing supinations and thus avoiding the swaying.

Figure 7:
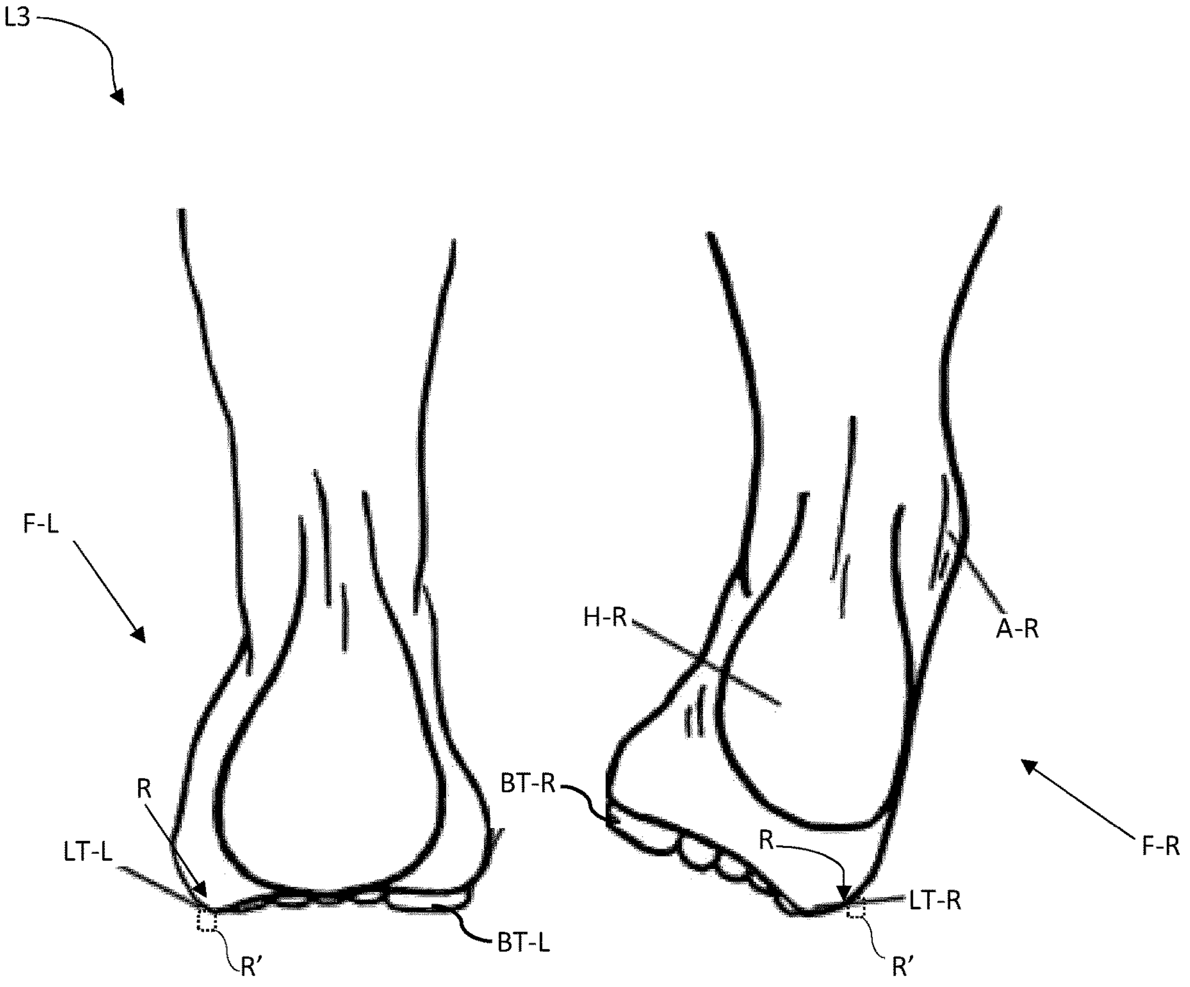
FIG. 7 is a rear view of human feet during over supination.

Turning back to FIG. 7, when the right foot F-R in over supination, the support element 168 would be positioned in region R' which would interface with region R thus stabilizing the the foot F-R from over supination. This position of the support element 168 is better shown in region R' on the left foot F-L of FIG. 7 which engagingly interfaces with the region R of the foot F-L.

In an embodiment, the support element 174 comprises a rectangular bar. In an embodiment the support element 174 has a length from about 8 mm to about 18 mm. In an embodiment, the support element 174 is made of rigid material. In an embodiment, the support element is made of high-density material. In an embodiment, the support element 174 has a width of about 10 mm to about 20 mm. In an embodiment, the support element 174 has a length of about 20 to about 40 mm.

Figure 16:
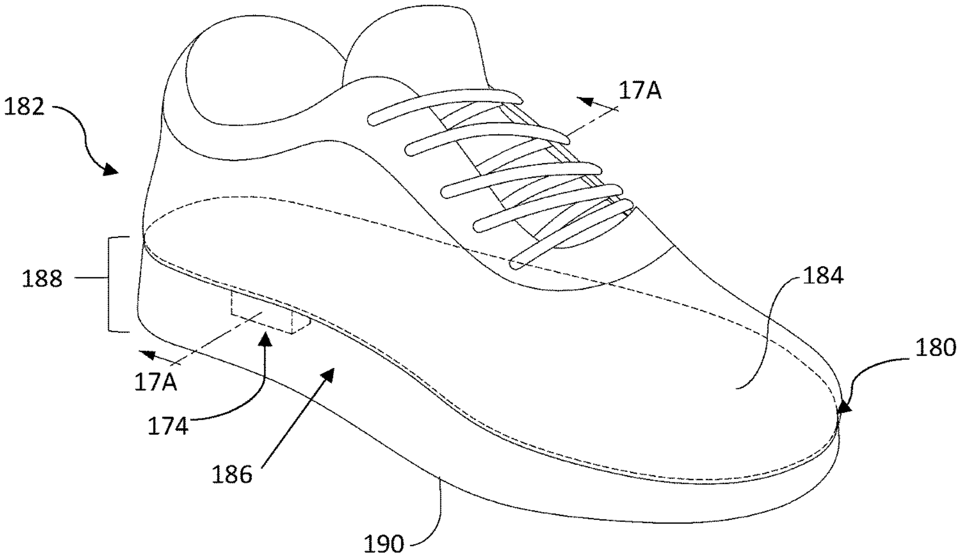
FIG. 16 is a perspective view of an inner sole structure integrated to footwear in accordance with another illustrative embodiment of the present disclosure.
Figure 17A:
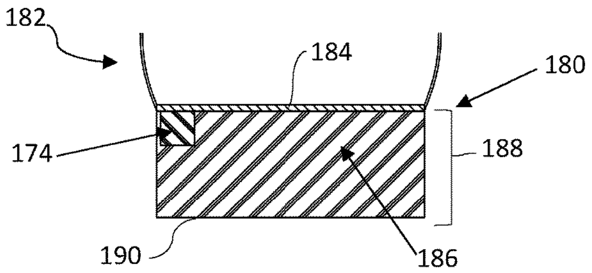
FIG. 17A is a cross sectional view of FIG. 16 taken along line 17A-17A thereof.
Figure 17B:
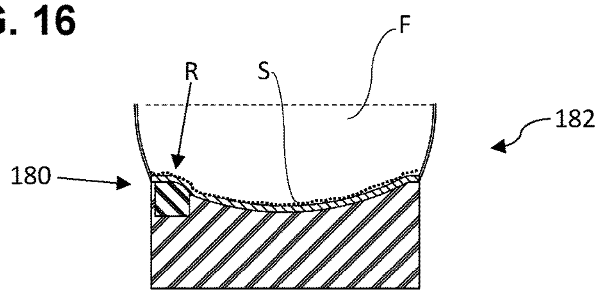
FIG. 17B is the cross sectional view of the footwear of FIG. 17A worn by the foot of a user in accordance with an illustrative embodiment of the present disclosure.

With reference to FIGS. 16, 17A and 17B, there is shown an inner sole structure 180 that is integrated into the footwear 182. The inner sole structure 180 comprises a top part or insole 184 overlying a bottom part 186 which is the inner part of the sole 188 defining the outer sole 190. The inner sole structure comprises the support element 174 integrated within the inner part 186 of the sole 188. FIG. 17A shows the position of the inner sole structure 180 when not use and FIG. 17B shows the position of the inner sole structure 180 when engaged by a foot F. The weight pushes the insole 184 inwardly into the inner sole part 186 with the support member 174 pushing upwardly against the sole S of the foot F at region R thereof which is the region corresponding to the anatomical area right behind the fifth metatarsal 39.

In an embodiment, the inner sole structure comprises the support element 174 herein positioned in the inner sole part of footwear.

The support element 174 provides for stabilizing the fifth metatarsal and extends to the front of the heel. The foregoing arrangement provides for controlling supinations or inversion of the foot and ankle thus preventing swaying. The foregoing arrangement provides for controlling subtalar and midtarsal joint motion which is required to stabilize the lateral ankle ligaments.

The various features described herein can be combined in a variety of ways within the context of the present disclosure so as to provide still other embodiments. Indeed, the support element 174 can be included into the inner sole structures 10, 10', 10" and 78 and 120. As such, the embodiments are not mutually exclusive. Moreover, the embodiments discussed herein need not include all of the features and elements illustrated and/or described and thus partial combinations of features can also be contemplated. Furthermore, embodiments with less features than those described can also be contemplated.

It is to be understood that the present disclosure is not limited in its application to the details of construction and parts illustrated in the accompanying drawings and described hereinabove. The disclosure is capable of other embodiments and of being practiced in various ways. It is also to be understood that the phraseology or terminology used herein is for the purpose of description and not limitation. Hence, although the present disclosure has been provided hereinabove by way of non-restrictive illustrative embodiments thereof, it can be modified, without departing from the scope, spirit and nature thereof and of the appended claims.

What is claimed is:

1. An inner sole structure for being mounted to footwear, the footwear comprising a footwear sole defining an outsole for engaging the ground and an inner sole part for supporting a foot of a footwear user, the inner sole structure providing for being mounted on the inner sole part of the footwear to be engaged by the foot, the inner sole structure comprising:

a top sole part defining a top side surface thereof, for being engaged by the foot of a footwear user, and an underside surface thereof for overlying the inner sole part of the footwear; and a middle sole part mounted to the underside surface of the top sole part, the middle sole part comprising an upper supple body layered on a lower rigid body, the upper supple body being mounted to the underside surface of the top sole part, the lower rigid body providing for engaging the inner sole part of the footwear, the middle sole part defining a U-shaped configuration with a front open end, a closed rear end, and a longitudinal channel devoid of any material therein extending between the front open end and the closed rear end, wherein when the inner sole structure is mounted to the inner sole part of the footwear and is engaged by the foot, the longitudinal channel under the foot is aligned with a longitudinal portion of the foot extending from a ball position of the foot to a heel position of the foot including an arch and a plantar fascia position of the foot, wherein the longitudinal portion of the foot engages the longitudinal portion of the top sole part along the longitudinal channel opening and the longitudinal channel thereby avoiding tension to the longitudinal portion of the foot, the lower rigid body providing support to the foot.

2. An inner sole structure according to claim 1, wherein a mid to rear section of the top sole part overlies the middle sole part and a front section of the top sole part does not overly the middle sole part and engages the inner sole wherein a mid to rear section of the top sole part overlies the middle sole part and a front section of the top sole part does not overly the middle sole part.

3. Ann inner sole section according to claim 2, wherein the front section of the top sole part engages the inner sole.

4. An inner sole structure according to claim 1, wherein the channel has a depth ranging from about 4 mm to about 12 mm.

5. An inner sole structure according to claim 1, wherein the channel has a width ranging from about 12 mm to about 24 mm.

6. An inner sole structure according to claim 1, wherein the channel has a constant width along a length thereof.

7. An inner sole structure according to claim 1, wherein a front area of the channel near the front open end defines a front channel width and a rear area of the channel near the rear closed end defines a rear channel width, wherein the front channel width is lesser than the rear channel width.

8. An inner sole structure according to claim 7, wherein the rear channel width is twice the front channel width.

9. A footwear comprising:

a footwear sole defining an outsole for engaging the ground and an inner sole part for supporting a foot of a footwear user; and an inner sole structure mounted on the inner sole part to be engaged by the foot, the inner sole structure comprising:

a top sole part defining a top side surface thereof, for being engaged by the foot of a footwear user, and an underside surface thereof overlying the inner sole part; and a middle sole part mounted to the underside surface of the top sole part, the middle sole part comprising an upper supple body layered on a lower rigid body, the upper supple body being mounted to the underside surface of the top sole part, the lower rigid body mounted to the inner sole part, the middle sole part defining a U-shaped configuration with a front open end, a closed rear end, and a longitudinal channel devoid of any material therein extending between the front open end and the closed rear end, wherein when the inner sole structure is engaged by the foot, the longitudinal channel under the foot is aligned with a longitudinal portion of the foot extending from a ball position of the foot to a heel position of the foot including an arch and a plantar fascia position of the foot, wherein the longitudinal portion of the foot engages the longitudinal portion of the top sole part along the longitudinal channel opening and the longitudinal channel thereby avoiding tension to the longitudinal portion of the foot, the lower rigid body providing support to the foot.

10. A footwear according to claim 9, wherein a mid to rear section of the top sole part overlies the middle sole part and a front section of the top sole part does not overly the middle sole part and engages the inner sole.

11. A footwear according to claim 9, wherein the channel has a depth ranging from about 4 mm to about 12 mm.

12. A footwear according to claim 9, wherein the channel has a width ranging from about 12 mm to about 24 mm.

13. A footwear according to claim 9, wherein the channel has a constant width along a length thereof.

14. A footwear according to claim 9, wherein a front area of the channel near the front open end defines a front channel width and a rear area of the channel near the rear closed end defines a rear channel width, wherein the front channel width is lesser than the rear channel width.

15. A footwear kit comprising:

a footwear comprising a footwear sole defining an outsole for engaging the ground and an inner sole part for supporting a foot of a footwear user; and an inner sole structure for being mounted on the inner sole part of the footwear to be engaged by the foot, the inner sole structure comprising:

a top sole part defining a top side surface thereof, for being engaged by the foot of a footwear user, and an underside surface thereof for overlying the inner sole part; and a middle sole part mounted to the underside surface of the top sole part, the middle sole part comprising an upper supple body layered on a lower rigid body, the upper supple body being mounted to the underside surface of the top sole part, the lower rigid body mounted to the inner sole part, the middle sole part defining a U-shaped configuration with a front open end, a closed rear end, and a longitudinal channel devoid of any material therein extending between the front open end and the closed rear end, wherein when the inner sole structure is mounted to the inner sole part of the footwear and is engaged by the foot, the longitudinal channel under the foot is aligned with a longitudinal portion of the foot extending from a ball position of the foot to a heel position of the foot including an arch and a plantar fascia position of the foot, wherein the longitudinal portion of the foot engages the longitudinal portion of the top sole part along the longitudinal channel opening and the longitudinal channel thereby avoiding tension to the longitudinal portion of the foot, the lower rigid body providing support to the foot.

16. A footwear kit according to claim 15, wherein a mid to rear section of the top sole part overlies the middle sole part and a front section of the top sole part does not overly the middle sole part and engages the inner sole.

17. A footwear kit according to claim 15, wherein the channel has a depth ranging from about 4 mm to about 12 mm.

18. A footwear kit according to claim 15, wherein the channel has a width ranging from about 12 mm to about 24 mm.

19. A footwear kit according to claim 15, wherein the channel has a constant width along a length thereof.

20. A footwear kit according to claim 15, wherein a front area of the channel near the front open end defines a front channel width and a rear area of the channel near the rear closed end defines a rear channel width, wherein the front channel width is lesser than the rear channel width.

* * * * *